(12) United States Patent
Rosskamp et al.

(10) Patent No.: US 7,977,310 B2
(45) Date of Patent: *Jul. 12, 2011

(54) METHOD FOR REDUCING CARDIOVASCULAR MORBIDITY AND MORTALITY IN PREDIABETIC PATIENTS AND PATIENTS WITH TYPE 2 DIABETES

(75) Inventors: Ralf Rosskamp, Gladstone, NJ (US); Hertzel Gerstein, Hamilton, CA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/140,598

(22) Filed: Jun. 17, 2008

(65) Prior Publication Data

US 2008/0287343 A1 Nov. 20, 2008

Related U.S. Application Data

(62) Division of application No. 10/757,201, filed on Jan. 14, 2004, now Pat. No. 7,405,196.

(60) Provisional application No. 60/439,941, filed on Jan. 14, 2003.

(51) Int. Cl.
*A61K 38/28* (2006.01)

(52) U.S. Cl. ........................................ 514/5.9

(58) Field of Classification Search .................. None
See application file for complete search history.

(56) References Cited

FOREIGN PATENT DOCUMENTS

| | | |
|---|---|---|
| EP | 1125560 | 8/2001 |
| WO | WO 01/80852 | 11/2001 |
| WO | WO 02/34259 | 5/2002 |

OTHER PUBLICATIONS

Yki-Järvinen et al. "Less Nocturnal Hypoglycemia and Better Post-Dinner Glucose Control With Bedtime Insulin Glargine Compared With Bedtime NPH Insulin During Insulin Combination Therapy in Type 2 Diabetes," Diabetes Care, 2000, 23, 1130-1136.*

Costa, A., et. al., Impaired Glucose Tolerance, Treat Endocrinol. 2002, vol. 1, pp. 205-210.

Nathan, D.M., et. al., Impaired Fasting Glucose and Impaired Glucose Tolerance: Implications for Care, Diabetes Care, 2007, 30(3), pp. 753-759.

Rosenstock, J., et. al., Basal Insulin Therapy in Type 2 Diabetes: 28-week Comparison of Insulin Glargine (HOE 901) and NPH Insulin, Abstract XP002282639 Medline, Diabetes Care Apr. 2001, vol. 24, No. 4, pp. 631-636.

Thomas, M., et. al. Evaluation of the Safety, Efficacy and Tolerability of Insulin Glargine in Subjects with Impaired fasting Glucose, Impaired Glucose Tolerance or New-Onset Type 2 Diabetes, Abstract Biosis/Biosis vol. 52, No. Supplement 1, 2003 pp. A451-A452 XP002282638.

Turner,R., et. al. Beta-Cell function Improved by Supplementing Basal Insulin Secretion in Mild Diabetes, British Medical Journal May 22, 1976, vol. 1, No. 6020, pp. 1252-1254 XP009031347.

Mooradian, A. D., et. al. , Cardiovascular Disease in Type 2 Diabetes Mellitus, Archives Internal Med., vol. 163, No. 1, pp. 33-40, (2003).

* cited by examiner

*Primary Examiner* — Christina Bradley (74) *Attorney, Agent, or Firm* — Oliver Loewrick; Scully, Scott, Murphy & Presser, P.C.

(57) ABSTRACT

This invention relates to a method of reducing cardiovascular morbidity and mortality in a prediabetic or Type 2 Diabetes patient population. The method comprises administering an effective dosage of a long acting insulin, preferably insulin glargine, to a prediabetic or Type 2 Diabetes patient.

10 Claims, 2 Drawing Sheets

METHOD FOR REDUCING CARDIOVASCULAR MORBIDITY AND MORTALITY IN PREDIABETIC PATIENTS AND PATIENTS WITH TYPE 2 DIABETES

CROSS REFERENCE TO RELATED APPLICATIONS

This application is a division of U.S. application Ser. No. 10/757,201, filed Jan. 14, 2004, now allowed, which claims the benefit of U.S. Provisional Application No. 60/439,941, filed Jan. 14, 2003, both of which are incorporated herein by reference in their entirety.

FIELD OF INVENTION

This invention relates to a method of reducing cardiovascular morbidity and mortality in a prediabetic or Type 2 Diabetes patient population.

BACKGROUND OF THE INVENTION

Diabetes Mellitus and Cardiovascular Disease

Patients with type 2 diabetes mellitus (DM) have an increased risk of atherosclerotic disease, including coronary heart disease, cardiovascular disease, and peripheral vascular disease. Diabetes itself[1] and not just the associated risk factors of dyslipidemia, hypertension, and obesity contributes a major portion of this risk. In particular, the level of hyperglycemia may play a key role. While the relationship of increased blood glucose to microvascular complications is well-recognized[7-9], its relation to atherogenesis was, until recently, less well documented. A prospective, population-based study in middle-aged and elderly patients in Finland with type 2 DM has shown a linear correlation between baseline fasting blood glucose (FBG), or $HbA_{1c}$, and coronary heart disease mortality[10]. In the WESDR database, subjects diagnosed with diabetes at age 30 years or older had a statistically significant increase in mortality from vascular causes for every 1% increase in glycosylated hemoglobin, with a hazard ratio of 1.10 to 1.28 for various types of events[11]. The Islington Diabetes Survey found a linear association between 2-hour postprandial glucose or $HbA_{1c}$ and coronary heart disease, with the stronger association with the 2-hour glucose test[12]. In the San Antonio Heart Study, the level of hyperglycemia was a strong, independent predictor of all-cause and cardiovascular mortality[13].

A growing body of evidence indicates that the increased risk for macrovascular complications associated with type 2 DM extends to patients with glucose abnormalities that do not meet the criteria for frank diabetes. The Hoorn study found an increased risk of all-cause and cardiovascular mortality with higher 2-hour post-load glucose values and increasing $HbA_{1c}$ in a non-diabetic general population of men and women[15]. In the EPIC study, an increase of 1% in $HbA_{1c}$ was associated with a 28% increase in risk of death and an increase of approximately 40% in cardiovascular or coronary heart disease mortality in a cohort of 4,662 men[4]. Although diabetic subjects were included in this trial, and diabetes was found to be an independent predictor of cardiovascular risk when evaluated separately from $HbA_{1c}$ (another independent predictor), only $HbA_{1c}$ and not diabetes predicted CV death when both were included in the same analysis, further strengthening the link between glucose elevations and CV risk, versus the presence or absence of diabetes. Similarly, a study in non-diabetic elderly women found that all-cause mortality and coronary heart disease were significantly related to fasting plasma glucose[16].

In a study from Oslo[17], non-diabetic men aged 40-59 years had a significantly higher cardiovascular mortality rate if their FPG was >85 mg/dL. Long-term follow-up of several prospective European cohort studies has confirmed a higher risk of cardiovascular-related mortality in non-diabetic men with the highest 2.5% of values of FPG and 2-hour postprandial glucose[18]. A meta-regression analysis of data from 20 cohort studies found a progressive relationship between glucose levels and cardiovascular risk even below the cutoff points for diagnosis of $DM^3$. Likewise, in the 23-year Paris Prospective Study[19] of 7,018 middle-aged nondiabetic men, increased fasting or 2-hour postprandial blood glucose was associated with increased total and coronary mortality in a graded, non-threshold relationship.

The American Diabetes Association (ADA) has recognized an intermediate category of IFG, defined as a fasting plasma glucose of 6.1-6.9 mmol/L (110-125 mg/dL)[6], as well as the older category of IGT, defined as a 2-hour glucose level of 7.8-11.1 mmol/L (140-199 mg/dL) after a 75 gram oral glucose load, with FPG levels below 7.0 mmol/L. The European Diabetes Epidemiology Group, based on a meta-analysis of 10 prospective European cohort studies, found that IGT was associated with survival curves intermediate between those of non-diabetic and diabetic subjects, while IFG curves were similar to those of normoglycemic subjects. A direct comparison revealed that IFG had a higher specificity (79%) for predicting cardiovascular disease than IGT (57%), but IGT was a more sensitive (54%) predictor than IFG (28%) in predicting incident cardiovascular disease[20].

In summary, the data cited above demonstrate that people with IFG and IGT (collectively referred to as "prediabetes") have an excess risk of development of overt type 2 diabetes, coronary heart disease, cerebrovascular disease, and peripheral vascular disease compared to a population with normal fasting and 2-hour postprandial glucose levels. Further, a continuum of increasing risk appears to exist, as opposed to a threshold level of hyperglycemia below which no increased risk prevails[2-4]. IGT and IFG subjects are currently unlikely to receive glucose-lowering treatment with existing pharmacotherapies. Their under-treated dysglycemia represents a large unmet medical need, and a large public health issue.

A number of large intervention studies have been conducted over the last two decades in both type 1 and type 2 diabetic patients. The primary aim of these trials was to evaluate the impact of improved metabolic control on microvascular endpoints and the studies were designed and sized accordingly.

Macrovascular outcomes were included in these trials as secondary endpoints and although the treatment differences seen were not statistically significant, trends were evident in each trial of an association between intensified glycemic control and reduced cardiovascular mortality and morbidity.

The two principal intervention trials in recent years were the Diabetes Control and Complications Trial (DCCT) in type 1 diabetic patients[7] and the United Kingdom Prospective Diabetes Study (UKPDS) in type 2 $DM^{14}$. In the DCCT, cardiovascular events decreased by 41% in the intensively-treated group, but this difference was not statistically significant. In the UKPDS, which compared the effects of intensive management to the effects of standard care on micro- and macrovascular complications in 3,642 type 2 diabetic subjects followed for a median of 10.4 years, a significant decrease in microvascular complications was observed in the intensive treatment group, which achieved a significantly lower median $HbA_{1c}$ of 7.0% compared to the standard group (median HbA$_{1c}$ 7.9%). Although strongly suggestive, the intervention data from this study failed to show a statistically significant decrease in the endpoint of myocardial infarction, which decreased by 16% with the 0.9% decrease in HbA$_{1c}$ (p=0.052). However, epidemiologic analysis of the UKPDS database[2] revealed that a single percent point decrease in HbA$_{1c}$ was associated with a 25% reduction in diabetes-related death, a 7% reduction in all-cause mortality, and an 18% reduction in fatal and nonfatal MI. Similar reductions in the risk for stroke, amputation and congestive heart failure were seen with decreasing HbA$_{1c}$. These associations of HbA$_{1c}$ with cardiovascular risk were without threshold, i.e. they occurred across the entire study population.

In the 8-year Kumamoto study[3] of intensive multiple-dose insulin treatment of type 2 diabetic patients, half as many serious macrovascular events (MI, angina, stroke, claudication, gangrene, or amputation) occurred in the intensive treatment arm as in the conventional treatment arm. This reduction was not statistically significant, in all likelihood because of the small size of the trial (n=110). Several large prospective trials, including the ACCORD trial (NHLBI) and the VA diabetes trial, are now ongoing or planned to specifically and primarily evaluate the hypothesis that treatment of diabetes in patients with cardiovascular risk factors will reduce cardiovascular morbidity and mortality.

Recent intervention studies in IGT have focused on the reduction of rates of progression to type 2 diabetes. Lifestyle interventions (primarily institution of diet and exercise plans) have led to striking reductions in progression from IGT to diabetes in both the recently-completed NIH-sponsored DPP in North America and the Finnish DPS lifestyle study. Each trial was terminated early after independently demonstrating a 58% reduction versus controls in development of new cases of type 2 DM from IGT in the lifestyle intervention arm[21,33]. Lifestyle changes were pursued aggressively in both studies, and whether such interventions can be maintained indefinitely is an open question.

Pharmacotherapies have also been tested in delaying the development of type 2 DM:

Metformin treatment of IGT in the DPP study was associated with a statistically significant 31% reduction in the rate of progression to type 2 DM.[21]

Acarbose in the STOP-NIDDM trial reduced the progression from IGT to type 2 DM from 41.8% in the placebo arm to 32.8% over 3.6 years' median duration of treatment (p<0.05) as well as reducing the risk of CV events by 49%.[40]

Troglitazone in the halted TRIPOD study; 12.3% of placebo-treated subjects versus 5.4% of troglitazone-treated subjects with prior gestational diabetes developed type 2 DM over a mean of 30 months of treatment (p<0.05).[45]

With the exception of the STOP-NIDDM study, cardiovascular risk reduction data from these recent diabetes prevention studies are all pending publication. At present the only other data available on CV risk reduction in the IGT/IFG population from treatment with pharmacologic antihyperglycemic agents come from a small Swedish study conducted in the 1960s which demonstrated a reduction in CV events in IGT subjects with the use of tolbutamide[22,23]. Clearly new therapies for glucose lowering must be tested for their effects on serious cardiovascular outcomes in this population.

Recent evidence has provided support for a beneficial effect of insulin treatment in improving cardiovascular outcomes in patients with diabetes. The DIGAMI study[24], in which diabetic patients hospitalized with acute MI were allocated to receive an IV insulin-glucose infusion in-hospital followed by intensive chronic outpatient treatment with insulin, versus standard treatment, showed a significant 28% reduction of all-cause mortality in the patients who received intensive insulin treatment. Most of these deaths were cardiovascular in etiology. The most striking reductions in mortality were seen in the subset of patients without prior insulin treatment, with low cardiovascular risk pre-MI. In those subjects significant survival differences were even seen pre-discharge, while still in hospital post-MI, and enhanced survival in the same cohort was also seen in long-term follow-up.

Part of the benefits of insulin treatment was likely due to improved long-term glycemia post-MI, but the in-hospital results suggest that other, more acute, effects of insulin besides long-term glycemic control may have played a role, such as improved platelet function, decreased PAI-I levels, and insulin-mediated reductions in circulating free fatty acid levels with consequent improved dyslipidemia and decreased myocardial oxygen requirement. Chronic insulin therapy may thus provide a level of protection against the cumulative deleterious effect of even subacute episodes of ischemia, and on the progression of atherosclerosis.

A recent study from Belgium[25] reinforces the beneficial role of insulin treatment of critically-ill subjects. In this trial, critical-care post-surgical patients with random blood glucose values greater than 110 mg/dL were treated while in ICU either with an insulin infusion to lower blood glucose to the 80-110 mg/dL range (intervention); or to receive insulin infusions only if blood glucose exceeded 215 mg/dL, with the aim of infusion to reduce blood glucose to between 180 and 200 mg/dL (control). Twelve-month follow-up showed significantly different reductions of 8.0% and 4.6% in overall mortality in the intervention and control groups respectively, and most of the benefit was attributable to the cohort of subjects who were in ICU for 5 days or more. In-hospital mortality, septicemia, acute renal failure and hemodialysis incidence, and transfusion requirements were also significantly reduced in the intervention group versus the control group.

The use of exogenous insulin in a IGT, IFG, or diabetic population should confer several potential metabolic and cardiovascular benefits associated with insulin treatment:

1. A powerful effect to delay the exposure of target tissues to toxic levels of glycemia that is finely titratable and durable, compared to oral antidiabetic agents.
2. Suppression of circulating free fatty acids (FFA) with:
    Reduced VLDL synthesis and improved lipoprotein patterns (lower triglycerides, increased HDL-C)
        Reduced lipotoxicity at the level of the beta cell and on insulin's target tissues
        Reduced obligatory oxidative metabolism in ischemic myocardium
3. Prevention of metabolic decompensation (including both glucose and FFA) due to stress, both mild and frequent (daily stresses and minor illness or injury) and severe and less common (major injury, illness, surgery, vascular events). These stress events will suppress endogenous insulin responses even when a pharmacologic secretagogue or sensitizer is present, but exogenous, injected insulin cannot be so suppressed.
4. In addition, recent work has demonstrated direct associations between insulin treatment and enhanced nitric oxide-mediated vasodilatation, which is impaired in insulin-resistant states such as IGT, IFG and diabetes 26, 27. Moreover, reductions in the endothelial dysfunction[28] and inflammation[29] that are characteristic of both diabetes and atherosclerosis have been demonstrated following insulin treatment.

Whereas insulin therapy is undoubtedly efficacious in reducing blood glucose concentrations and, as noted above, may hypothetically improve survival in individuals with dysglycemia, outcome studies using insulin in this population have not been done to date. Several reasons may account for this including a) the need for insulin to be injected as opposed to be taken orally; b) concerns regarding the side effect of hypoglycemia; (low blood glucose) c) epidemiologic evidence linking high serum insulin levels to macrovascular disease; d) the very recent recognition that glucose is a risk factor for cardiovascular outcomes across the range from normal through all stages of diabetes; e) lack of predictability in the action of long-acting insulins; and f) lack of experience in achieving near-normal glucose levels with insulin preparations available to date.

Many of these issues are, however, not relevant today. First, it is now widely recognized that the epidemiologic relationship between hyperinsulinemia and macrovascular disease is extremely unlikely to imply a cause-effect relationship. This is based on randomized controlled trial evidence from both the DCCT and the UKPDS trials that individuals who were given exogenous insulin in an effort to reduce the risk of microvascular disease had a trend towards fewer, not more, adverse cardiovascular outcomes. This conclusion is supported by other studies discussed above, including the DIGAMI study, the Kumamoto study, a meta-analysis of studies of intensified insulin therapy in type 1 diabetes, and several other analyses. It therefore appears that hyperinsulinemia as a result of exogenous administration of insulin is not a cardiovascular risk factor. Second, the potential of intensified insulin therapy has achieved new attention in light of the UKPDS and the potential benefits of tight glycemic control in people with type 2 diabetes. Third, the simplicity of glucose monitoring devices and the decreasing costs of home glucose monitoring, as well as the negligible discomfort associated with today's injection devices available today, have made injections and blood glucose monitoring more accessible and easier for patients to accomplish. Fourth, there is growing recognition of the importance of metabolic abnormalities as a cause of cardiovascular disease. Finally, there are new long acting analog insulins having properties such as a longer duration of action (up to 24 hours) and a smoother profile, with a less defined peak of action which make them viable treatment agents in the IGT, IFG early Type 2 diabetes populations.

Lantus® LANTUS (insulin glargine) is a recombinant human insulin analog that is a long-acting (up to 24-hour duration of action), parenteral blood-glucose lowering agent.[39] The post-marketing surveillance safety database experience reveals no increased incidence of hypoglycemia or unexpected adverse reactions compared to other marketed insulin preparations. In a multiple-dose pharmacokinetic study, Lantus® LANTUS (insulin glargine) levels were shown to reach steady-state after 2 doses (2 days) of treatment (Study 1020). Treatment with Lantus® LANTUS (insulin glargine) insulin offers the possibility of a smooth, daylong, blood insulin profile without a definite peak that can be finely titrated to lower subjects' FPG in a durable manner, while minimizing the risk of hypoglycemia at other times of day.

However, a central question concerns the administration of insulin to nondiabetic or early diabetic subjects and the propensity for hypoglycemia this may confer. Insulin has traditionally been reserved for treatment of more severe hyperglycemia, in established type 1, or advanced type 2, diabetes. In these patients the risk of hypoglycemia is greater the closer the achieved blood glucose is to normal.[42]

For type 2 diabetic patients, as well as individuals with prediabetes, medical management begins with diet restriction and exercise as tolerated[30,31]. Even if pharmacotherapy in the form of oral antidiabetic drugs or insulin is needed later, diet and exercise are always the cornerstone of disease management. No drugs are currently approved for the treatment of prediabetes, but most of these individuals are overweight or obese, and successful lifestyle intervention has been shown to improve blood glucose levels and even delay progression to diabetes[32,33]. Exercise increases blood glucose uptake in muscle, and leads to a reduction in endogenous insulin output, as little insulin is needed to provide fuel to these tissues during exercise.[34] Exogenous, pharmacologically-provided insulin present in the circulation cannot be so modulated, and its presence can predispose to hypoglycemia.

Exercise-induced hypoglycemia in insulin-treated diabetes patients is well-described[35,41], and is often dealt with in practice by reducing the mealtime insulin dose, or giving oral calories, prior to an exercise session.[36,37] These methods are cumbersome, and hypoglycemia is still a risk following exercise. The insulin dose that is most frequently modulated in response to upcoming exercise is the short-acting insulin given before the preceding meal, because these insulins have prominent peaks in their actions, used to target the blood glucose rise that occurs following a meal, but they place patients at increased risk for hypoglycemia if there is a mismatch between insulin availability and calories absorbed. Thus hypoglycemia is a risk for all insulin-treated individuals, and this risk is enhanced when these individuals exercise, and the closer to normoglycemia they are treated.

The ideal basal insulin might be expected to be less worrisome from this standpoint because the circulating insulin produced would target blood glucose elevations throughout the day rather than mealtime fluctuations. It would not demonstrate notable peaks in plasma level, and in consequence the tendency to produce hypoglycemia would be less than with peaked insulins. The "Treat-to-Target" study[38] in US/Canada type 2 diabetic patients investigated whether a single bedtime dose of Lantus® LANTUS (insulin glargine) vs. NPH insulin (a moderate- to long-acting insulin with a pronounced peak in plasma activity for 4 to 8 hours after injection)[39] would achieve target metabolic control without increasing nocturnal hypoglycemia. The trial was successful in demonstrating both its primary objective (more Lantus® LANTUS (insulin glargine)-treated patients than NPH-treated patients reaching target HbAlc [<=7%] without nocturnal hypoglycemia), but also showed significant reductions in nocturnal hypoglycemia vs. NPH in all patients.

If peaked insulins pose a danger for hypoglycemia in advanced type 2 diabetes, they certainly do in milder forms of diabetes, and in prediabetes, where the blood glucose concentrations are only modestly elevated, especially in relation to exercise. Treatment with an insulin with notable peak effects runs a great risk of producing low blood glucose levels that will be bothersome and dangerous to people with these conditions. There exists an unmet medical need to provide insulin treatment to individuals with milder glucose intolerance who are at high risk for CV disease. Cardiovascular disease in subjects with IGT, IFG, and early diabetes is prevalent and life-threatening. Advances have been made in recent years in treating the associated cardiovascular risk factors of hypertension and hyperlipidemia. Depended upon the results of the morbidity/mortality study association between blood glucose elevations and cardiovascular risk in these subjects is likewise continuous and progressive, treatment of this dysglycemia becomes urgent.

Insulin treatment has been demonstrated to reduce CV morbidity and mortality in a population with more advanced diabetes, and offers this prediabetic population the possibility of reducing cardiovascular risk through effective reductions in blood glucose and free fatty acid levels, and in the associated tissue damage resulting from their chronic elevations. The availability of Lantus® insulin LANTUS (insulin glargine) creates the possibility of treating subjects with widely-varying degrees of dysglycemia with the effectiveness of insulin over a 24 hour period while minimizing the risk of hypoglycemia (especially hypoglycemia seen in association with exercise) inherent in earlier insulin preparations with more distinct peak effects.

Diabetic dyslipidemia (DDL) in type 2 diabetes is another condition where there exists an unmet medical need. DDL is characterized by fasting hypertriglyceridemia, low HDL cholesterol (HDL-C), small dense (atherogenic) LDL particles, and elevated free fatty acid (FFA) concentrations. Whereas lipid disorders associated with type 1 diabetes (hypertriglyceridemia with low LDL) are simpler in etiology, and relate to insulin deficiency which, when replaced, normalizes the plasma lipid profile, the pathophysiology of lipid disturbances in type 2 diabetes is more complex, being partly related to concomitant obesity and insulin resistance. Key factors in the development of lipid abnormalities in type 2 diabetes include:

- Failure of suppression of hormone-sensitive lipase in adipose tissue, which leads to increased lipolysis and increased supply of FFA from the adipocyte for, among other things, VLDL-triglyceride (TG) synthesis by the liver
- Reduced catabolism of TG-rich particles (such as VLDL), and reduced transfer of surface components of those particles to HDL, partly accounting for the low HDL-C levels seen in DDL.
- Accelerated transfer of cholesterol from HDL to other lipoproteins, also contributing to low HDL-C
- Reduced clearance of chylomicrons and more atherogenic chylomicron remnants, as well as reduced clearance of other remnant particles (intermediate-density lipoproteins or IDL)
- Decreased activity of lipoprotein lipase (LPL) and hepatic TG lipase (HTGL) which break TG down into FFA for fuel in muscle and fat cells.
- Overproduction of VLDL by the liver, exacerbated by elevations in glucose and FFA Although the lipid abnormalities of type 2 diabetes are more resistant to normalization with antidiabetic treatment, even when that treatment is successful, increased insulinization has been shown to improve most of the defects above, namely, improved lipase activity with reduced lipolysis; increased clearance of chylomicrons; reduced production of VLDL from the liver, both through reduction of FFA substrate and by independent mechanisms; and increases in HDL, generally seen in association with increased LPL activity.

The treatment initially recommended for type 2 diabetes, and reinforced as the cornerstone of management even after pharmacologic treatment is initiated, is diet control and regular exercise. When these lifestyle measures are no longer successful alone in controlling blood glucose levels, pharmacologic treatment is begun, traditionally using oral antidiabetic drugs alone and in combination. Whereas there is no a priori reason why insulin cannot be used to manage mildly diabetic patients, it is usually reserved for late-stage diabetes management because:

- Insulin must be given by injection and many patients find injections objectionable
- Insulin and injections have acquired the stigma of late-stage management—"if I'm taking insulin my diabetes must be very severe"—and to forestall insulin is a way of saying "my diabetes isn't so bad yet"

In fact insulin injections have become almost painless in recent years due to improved delivery systems. The "late-stage" stigma is based on tradition and former practice more than any real reason why insulin should be reserved for the end game of diabetes.

The one valid reason for not using insulin in patients as first pharmacotherapy is a concern over the one principal side effect of insulin—low blood glucose, or hypoglycemia. This is an important concern in using insulin to treat early type 2 diabetes primarily because most available insulins have a peak in their plasma activity at a certain time following injection. It is at these times of peak activity that the insulin-treated patient with diabetes is most vulnerable to hypoglycemia, and diets and exercise patterns must often be tailored around the prescribed insulin regimen to avoid hypoglycemia. This risk is greater the closer patients' blood glucose levels come to normal—and yet normoglycemia is the goal of diabetes management.

There is evidence that the scientific community is taking the abnormalities of DDL more seriously than it has in the past in terms of the risk they pose for atherogenesis. The Adult Treatment Panel of the NCEP on the "detection, evaluation, and treatment of cholesterol disorders in adults" authored an update of the ATP II summary in the Fall of 2002. The ATP III took hypertriglyceridemia more seriously than the predecessor ATP II Committee had as a marker for increased CV risk. The ATP III acknowledged that more recent studies, and additional analyses of older studies, have shown elevated TGs to be an independent risk factor for CHD, whereas in the past the association between TG and CHD was not independent from other confounding risk factors such as LDL and HDL abnormalities. ATP III reduced the TG concentration threshold for each degree of abnormality (normal, borderline, high, and very high) from their ATP-II levels, and offered VLDL cholesterol, and serum TG, as markers for atherogenic remnant lipoproteins, which the committee identified as a target for intervention as well as LDL-C. The committee formalized the concept of "non-HDL cholesterol" (non-HDL-C) as a target for therapy in persons with hypertriglyceridemia, perhaps more relevant than LDL-C alone in these individuals. Non-HDL-C was seen as an acceptable surrogate for apo-B in routine clinical practice.

ATP III pointed out that when fasting TG are less than 200 mg/dL, VLDL-C is not markedly elevated, and non-HDL-C correlates very well with LDL-C. As TG rises above 200 mg/dL, the relation between LDL-C and non-HDL-C is looser, and LDL-C alone "inadequately describes the CV risk associated with atherogenic lipoproteins." When fasting TG exceed 500 m/dL, much of the cholesterol resides in non-atherogenic forms of TG-rich lipoproteins, and non-HDL-C becomes "less reliable as a predictor of CHD risk." On the other hand, the risk of markedly elevated TG (>500 mg/dL) for pancreatitis has long been recognized, even by FDA, and here too the ability of insulin to reduce these elevations may exceed what other OADs can deliver. Thus there are two categories of elevations in fasting TG that may be amenable to insulin treatment, and for which insulin may be superior to OADs. One is elevations in the 500-1000 mg/dL range, for which hypertriglyceridemia alone is the target, being a surrogate for reduction in risk for pancreatitis. The other is elevations in the 200-500 mg/dL range, for which hypertriglyceridemia is one of a host of biomarkers associated with

SUMMARY OF THE INVENTION

The present invention provides a method of treating IGT in a patient comprising administering an effective dosage of a long acting insulin.

The present invention also provides a method of treating IFG in a patient comprising administering an effective dosage of a long acting insulin.

The present invention also provides a method of treating Type 2 diabetes, particularly early Type 2 diabetes, in a patient comprising administering an effective dosage of a long acting insulin.

The present invention also provides a method of treating diabetic dyslipidemia in a Type 2 diabetes patient comprising administering an effective dosage of a long acting insulin.

The present invention also provides a method of treating atherosclerosis in a patient with a disease or condition selected from the group of IFG, IGT or Type 2 diabetes, particularly early Type 2 diabetes, comprising administering an effective dosage of a long acting insulin.

The present invention also provides a method of improving endothelial function in a patient diagnosed with a disease or condition selected from the group of IFG, IGT or Type 2 diabetes, particularly early Type 2 diabetes, comprising administering an effective dosage of a long acting insulin.

The present invention also provides a method of preventing an increase in left ventricular mass in a patient diagnosed with a disease or condition selected from the group of IFG, IGT or Type 2 diabetes, particularly early Type 2 diabetes, comprising administering an effective dosage of a long acting insulin.

The present invention also provides a method of improving left ventricular diastolic and systolic function in a patient diagnosed with a disease or condition selected from the group of IFG, IGT or Type 2 diabetes, particularly early Type 2 diabetes, comprising administering an effective dosage of a long acting insulin.

The present invention also provides a method of preventing an increase in carotid intimal thickness in a patient diagnosed with a disease or condition selected from the group of IFG, IGT or Type 2 diabetes, particularly early Type 2 diabetes, comprising administering an effective dosage of a long acting insulin.

The present invention also provides a method of reducing blood glucose levels in a patient diagnosed with a disease or condition selected from the group of IFG, IGT or Type 2 diabetes, particularly early Type 2 diabetes, comprising administering an effective dosage of a long acting insulin.

The preferred long acting insulin for each of the above methods is insulin glargine.

DETAILED DESCRIPTION OF THE INVENTION

Study HOE901-1021 was conducted to test the safety, efficacy, and tolerability of Lantus® LANTUS (also known as HOE901 and insulin glargine) in treating individuals with IGT, IFG, and mild diabetes. As stated earlier, this patient population is at high risk for CV disease.

Study HOE901/1021 was a randomized, single-blind (pharmacist-unblinded), inpatient, dose-titration study designed to examine the safety and efficacy of HOE901 given once a day subcutaneously at bedtime in a novel population: people with impaired glucose tolerance (IGT) or impaired fasting glucose (IFG). It was conceived as a pilot study for a large international trial of HOE901 in a dysglycemic population of IGT, IFG, and early type 2 diabetes in order to investigate dosing in the prediabetic (IFG/IGT) population for the first time. Of special interest was the incidence of hypoglycemia during the study.

The study was conducted at three centers in the US. After screening tests, including fasting plasma glucose (FPG) and post prandial plasma glucose (PPG; two hours following a 75 g oral glucose load) for classification as IGT, IFG, diabetic, or normal glucose tolerance (NGT), and after satisfying other inclusion criteria including the ability to perform moderate exercise on a stationary bicycle, subjects were admitted to an inpatient study center. They were confined there for the next 15 days, during which time they were randomly assigned to receive either HOE901 once per day subcutaneously in the evening, or matching placebo (saline) injections in a 3:1 randomization (HOE901:placebo). Baseline assessments included a 5-point (before each meal, bedtime, and 3 AM) and 8-point (5-point plus readings 2 hours after each meal) blood glucose profile on separate days, and 15 minutes of exercise on a stationary bicycle at a level of exertion of "somewhat hard" on the Borg scale with blood glucose values monitored during and for 3 hours following the exercise. Each subject received a 25 kCal/kg diet while confined in the study center. Capillary whole blood glucose values were recorded on HemoCue devices. Episodes of hypoglycemia (blood glucose $\leq$50 mg/dL [2.8 mM] or symptoms with blood glucose $\leq$65 mg/dL [3.6 mM]) were recorded.

Once randomized, subjects' bedtime doses of study drug were titrated to achieve a fasting blood glucose (FBG) of 80-95 mg/dL [4.4 mM-5.3 mM]. Dose increases were based on FBG values and were performed every 2 days. Subjects remained at the site until the end of the confinement period, regardless of when target FBG levels were achieved. Five-point blood glucose profiles were performed every other day, with 8-point blood glucose profiles performed on alternate days. At endpoint all baseline procedures, including an 8-point blood glucose profile, and an exercise assessment, were repeated.

Subjects were treated from 18 Feb. 2002 to 17 Apr. 2002. Data from the study are still being analyzed, but principal results of the study are summarized below.

Twenty-one subjects were enrolled into the study. Two discontinued before completion: 1 HOE901 subject due to hypoglycemia, who however, never received study drug, and 1 subject withdrew prior to randomization. Nineteen subjects completed the study, 15 in the HOE901 group and 4 in the placebo group. The table below summarizes the demographic and baseline characteristics of these subjects.

| Demography and baseline characteristics |||| 
|---|---|---|---|
| Characteristic | Placebo | HOE901 | All |
| Female | 4 (80.0%) | 6 (37.5%) | 10 (47.6%) |
| Male | 1 (20.0%) | 10 (62.5%) | 11 (52.4%) |
| Mean age (yrs) | 54.6 | 54.8 | 54.7 |
| Median age (yrs) | 53.0 | 52.0 | 53.0 |
| Mean BMI (kg/m2) | 31.2 | 30.7 | 30.8 |
| Number (%) of subjects with: | | | |
| IGT/IFG | 2 (40.0%) | 7 (43.8%) | 9 (42.9%) |
| Type 2 diabetes | 3 (60.0%) | 7 (43.8%) | 10 (47.6%) |
| NGT | 0 (0.0%) | 2 (12.4%) | 2 (9.5%) |
| Mean screening values for: | | | |
| FPG (mg/dL) | 114 | 110 | 111 |
| PPG (mg/dL) | 212 | 192 | 197 |

Although it was intended to enroll only IGT/IFG subjects, difficulties in locating enough of these subjects in the timeframe allotted for enrollment necessitated the inclusion of subjects who were found to be diabetic at screening (none were known to be diabetic prior to the study). Two subjects were enrolled with NGT (FPG and PPG of 100 and 133, and 95 and 135 mg/dL, respectively).

The starting dose following randomization for all subjects was initially set at 6 IU. Because of the occurrence of hypoglycemia in 2 subjects at this dose, the starting dose was reduced to 4 IU. The mean dose at endpoint (Day 12) was 8.4 IU for HOE901 (0.096 IU/kg), and 17.0 IU (0.195 IU/kg) for placebo.

All but 2 subjects in the HOE901 group had reached an FPG of 100 mg/dL by Day 12, and all but 4 had reached the FBG target of 95 mg/dL or less.

Figure 1:
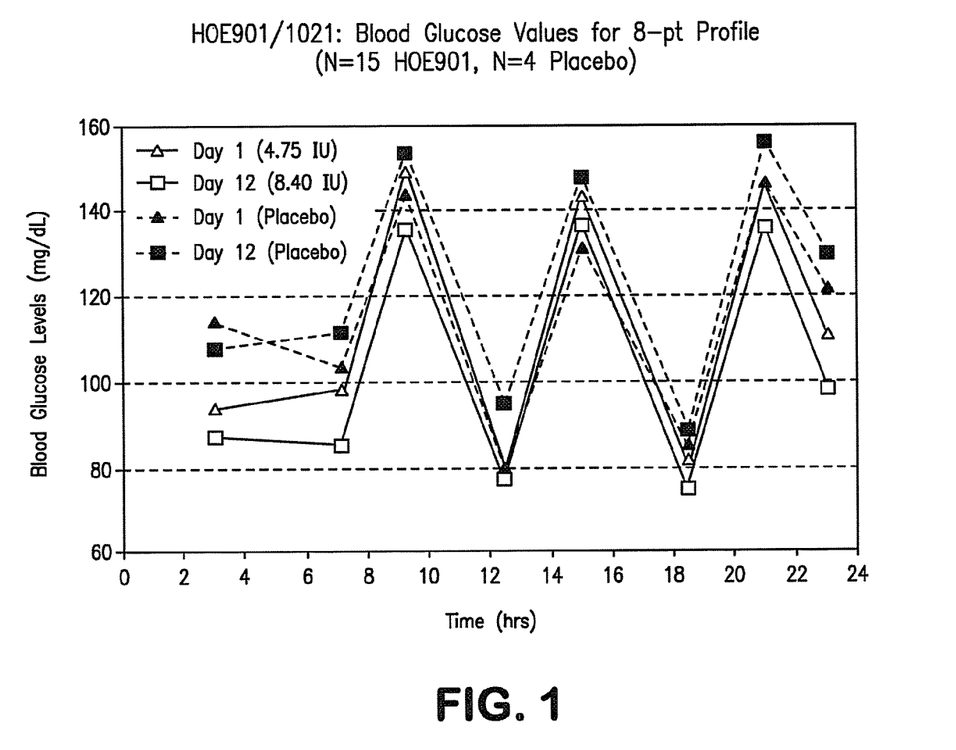
FIG. 1 depicts mean blood glucose values on the 8-point profiles at Day 1 (baseline) and Day 12 (endpoint).

FIG. 1 displays the mean blood glucose values on the 8-point profiles at Day-1 (baseline) and on Day 12 (endpoint). As seen, there were small reductions from baseline to endpoint in mean blood glucose concentrations in the HOE901 group, ranging from 2.0 to 13.3 mg/dL at different time points. Mean FBG was reduced from 98.1 to 85.6 mg/dL, and mean daylong blood glucose was reduced by 8.8 mg/dL, in the HOE901 group. In the HOE901 group the lowering of blood glucose from Day-1 to Day 12 was not confined to the fasting time point, but occurred daylong, at each time point.

In contrast, in the placebo group mean blood glucose values increased at most time points, with a mean FPG increase from 103.8 to 111.3 mg/dL and a mean daylong blood glucose increase of 8.2 mg/dL. The placebo group mean response was heavily influenced by 1 of the 4 subjects who had large increases in 8-point blood glucose over the course of the study, for unclear reasons.

It is clear from these data and the mean screening values in the table above that there was a drop in mean fasting glucose in the HOE901 group between screening and Day-1 (baseline). Differences in blood glucose measurements (plasma at screening, whole blood at Day-1) contributed to the observed drop in blood glucose between these two time points, however, the likely reason for most of this difference was the institution of a diet policy in both groups (in this study a diet similar to what would be prescribed in these subjects in practice (25 Kcal/kg) was used). Diet compliance in subjects with dysglycemia is classically poor, but because the subjects were confined in this study, they were perforce adherent to the diet regimen, and it was effective in lowering their blood glucose levels. No such decrease in mean FBG occurred between screening and Day-1 in the 5 subjects taking placebo. Mean body weight was reduced in both the placebo group and HOE 901 over the course of the study, by 0.25 and 0.44 kg respectively.

Figure 2:
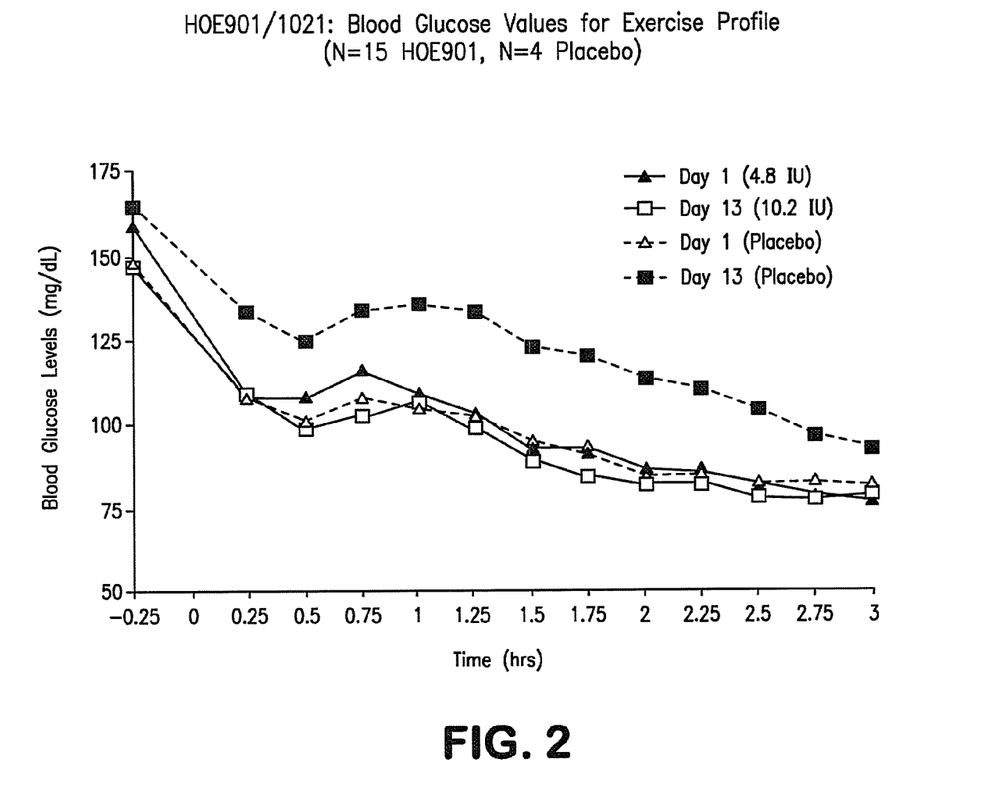
FIG. 2 illustrates mean blood glucose responses before (0.25 hr) and for 3 hours following the 15 minute stationary bicycle exercise period.

FIG. 2 below illustrates mean blood glucose responses before (−0.25 hr) and for 3 hours following the 15-minute stationary bicycle exercise period. As can be seen, mean blood glucose was similar before and after treatment with HOE901, and did not approach the hypoglycemic range. In the placebo group mean blood glucose showed a notable increase from Day-1 to Day 12, due to 2 of the 4 subjects in that group who demonstrated large increases over baseline by Day 12, for reasons which are unclear but are possibly related to relative physical inactivity over the 2 weeks of confinement, with resultant decreased insulin sensitivity at the time of the assessment on Day 12. It is noteworthy that no hypoglycemic events were reported during exercise for any subject.

Treatment-emergent adverse events (TEAEs) occurred in 10 subjects in the HOE901 group (16 events) vs. 2 in the placebo group (5 events). Each event occurred in only 1 individual except for headache, which occurred in 3 HOE901 subjects. Only 2 HOE901 subjects and 1 placebo subject had events that were considered by investigators as possibly related to study drug. The HOE901 events were 2 episodes of headache, and one of hypoglycemia. The two headaches occurred in subjects who had hypoglycemic events on the same days and at approximately the same time as the headaches. There were no serious adverse events during the study. Subject 3011 (who reported dizziness as an adverse event during screening) was removed from the study by the sponsor prior to receiving any study drug dose because of hypoglycemia that occurred during screening.

HOE901 treatment plus modest calorie restriction was effective in lowering blood glucose values in these dysglycemic individuals to target FBG levels. Daylong (8-point) blood glucose profiles were lowered in parallel to FPG in the HOE901 group. A relatively low dose of HOE901 (mean of only 8.4 IU) was required to achieve the glucose goals under these test conditions. Blood glucose profiles in response to exercise fell only modestly over the course of the study in the HOE901 group. Blood glucose responses in the placebo group increased over the course of the study in both 8-point and exercise assessments, but the small size of this group and the atypical responses of 1 or 2 subjects makes drawing conclusions from the placebo responses difficult.

Only mild hypoglycemia occurred in 4 out of 16 subjects treated with HOE901 in this study. These hypoglycemic events generally occurred before lunch or supper, and resolved promptly with oral caloric intake. No episodes of hypoglycemia occurred in relation to exercise. Although the calorie-restricted diet subjects consumed during this study doubtless played a role in the occurrence of these events, the diet was typical in size for what is recommended to these frequently overweight individuals. Based on this study in individuals with IGT, IFG, or mild untreated type 2 diabetes, the administration of HOE 901 seems safe and well tolerated. Hypoglycemia can occur, but is manageable not related to exercise, and detectable with the aid of home glucose monitoring.

Thus in this study it was possible to use Lantus® LANTUS (insulin glargine) to treat the mildly hyperglycemic subjects to normoglycemic levels without hypoglycemia in relation to exercise. These data have prompted the undertaking of a large intervention trial, the ORIGIN study, wherein it is expected that Lantus® LANTUS (insulin glargine) will be shown to be efficacious in reducing CV disease, with low risk for producing hypoglycemic side effects in relation to the exercise which forms a cornerstone of the glucose management of these individuals. The ORIGIN study will randomly allocate approximately 10,000 subjects with IGT, IFG, or early type 2 diabetes at risk for cardiovascular morbidity (because of a history of previous serious cardiovascular events, or because of significant cardiovascular risk factors) either to treatment with a single injection of Lantus® LANTUS (insulin glargine) per day, titrated to produce a FPG of 95 mg/dL or less without hypoglycemia, or to standard treatment of each condition. Examples of serious cardiovascular events include, but are not limited to, previous myocardial infarction, stroke, angina with documented ischemic changes, previous coronary, carotid or peripheral arterial revascularization, or left ventricular hypertrophy by electrocardiogram or echocardiogram. Examples of significant cardiovascular risk factors include, but are not limited to, previous myocardial infarction, stroke, angina with documented ischemic changes, previous coronary, carotid or peripheral arterial revascularization, or left ventricular hypertrophy by electrocardiogram or echocardiogram. This standard treatment plan includes a stepped-care algorithm for the institution of therapy in subjects who are either diabetic at baseline, or who become so during the trial. Monitoring of, and treatment intervention in, these control subjects will occur in a manner that is at least as aggressive as that recommended by currently-accepted standards of care (e.g. ADA guidelines). The morbidity/mortality study will be multicenter, international, randomized, and open-label, with a mean treatment duration of 5 years. The primary outcome variable is a composite cardiovascular endpoint of cardiovascular deaths, nonfatal MI and stroke, revascularization, hospitalization for heart failure CHF, and unstable angina. Secondary variables include all-cause mortality and rates of development or progression of microvascular disease. A separate investigation will examine the progression to type 2 diabetes in the IGT and IFG subjects treated with Lantus® LANTUS (insulin glargine) versus usual care.

Despite the novelty of the treatment paradigm proposed for the ORIGIN study, it is believed that hypoglycemia will be minimal based on several factors:

1. The 24-hour plasma insulin profile without a definite peak resulting from Lantus® LANTUS (insulin glargine) administration, decreasing the vulnerability of patients to excessive insulin concentrations which have historically occurred at unpredictable times during the day, and to unpredictable degrees, with other insulin preparations.
2. The gradual dose titration scheme proposed for the study. Lantus® LANTUS (insulin glargine) doses will start low, from 2-6 IU per day and the insulin administered will be distributed over a 24-hour period. Dose increases will be small, and made only after FPG levels from previous doses have reached steady-state.
3. The goal of Lantus® LANTUS (insulin glargine) titration is a target FPG of 95 mg/dL. This is at the upper end of the normal range for subjects without diabetes. Many IGT subjects in this trial will have an FPG in the target range from the start of the study, and if assigned to receive Lantus® LANTUS (insulin glargine) will consequently receive the starting dose only. In any case, the risk of nocturnal hypoglycemia resulting from Lantus® LANTUS (insulin glargine) administration which has reduced FPG to the vicinity of 95 mg/dL should be minimal, especially since most of these subjects will exhibit a degree of decreased insulin sensitivity.
4. Subjects will be asked to monitor their blood glucose at home especially during titration, to detect any tendency to hypoglycemia in that setting (peri-exercise, after missed meals, overnight).

The results of the 1021 Study which confirmed the safety and tolerability of Lantus® LANTUS (insulin glargine) in drug-naïve type 2 diabetes patients as well as in prediabetic individuals, also support Lantus' LANTUS' (insulin glargine) special usefulness in patients with moderate to severe DDL.

Insulin has features that make it especially useful in the patient with pronounced diabetic dyslipidemia, as compared to the oral antidiabetic agents usually used as initial pharmacotherapy. The "Treat-to-Target" study (HOE901/4002) of Lantus LANTUS (insulin glargine) in a type 2 diabetic population inadequately treated with oral drugs was notable in demonstrating the success of Lantus LANTUS (insulin glargine) and its comparator, NPH insulin, in reducing blood glucose levels to target levels in the majority of randomized patients. NPH insulin despite having a prolonged duration of action, has a pronounced peak effect from 3-6 hours after injection, rendering it less suitable in the management of the patient with milder diabetes due to the risk for hypoglycemia. Indeed even in this more severely diabetic population Lantus LANTUS (insulin glargine) demonstrated significant advantages over NPH in hypoglycemia, especially nocturnal hypoglycemia.

As a consequence of the excellent glycemic control attained, which set the standard for glycemic control in future trials, the 4002 study results are especially useful as an assessment of Lantus's LANTUS (insulin glargine) effects on lipids. The effects of Lantus LANTUS (insulin glargine) in the population of the "treat-to-target" 4002 study on fasting TG levels increased with the magnitude of baseline TG elevations: reductions of 24%, 34%, and 38% were seen in fasting TG levels with, respectively, all patients; those with fasting TG in the 300-499 mg/dL range (13% of the 4002 population); and those with elevations of 500 mg/dL or more (another 8% of the 4002 population). It is also notable that highly statistically significant reductions in non-HDL-cholesterol (see below) were seen in the two pooled treatments in the 4002 study, greater in magnitude the higher the baseline level of TG.

There is evidence from the literature that use of sulfonylurea (SU) as initial drug treatment of the type 2 patient with DDL exerts a weaker effect on reduction of hypertriglyceridemia, or on increasing HDL-C, than is seen with insulin, and/or that the effects are less durable. In order to compare the effects of Lantus LANTUS (insulin glargine) on fasting TG and non-HDL-C levels with oral agents from the sulfonylurea class, the glimepiride (Amaryl® AMARYL) database at Aventis was examined. Both multicenter placebo-controlled studies in the Amaryl® AMARYL (glimepiride) registration database demonstrated a more modest effect of Amaryl® AMARYL (glimepiride) on both TG and non-HDL-C concentrations than Lantus LANTUS (insulin glargine) demonstrated in the 4002 study, despite a prominent effect of Amaryl® AMARYL (glimepiride) to lower blood glucose. These results are shown in Table 1 below for patients with various levels of fasting hypertriglyceridemia.

TABLE 1

Summary of lipid data for LANTUS (from 4002 Study) and AMARYL (from two AMARYL studies with placebo control)

| Variable | Subgroup by TG baseline range | Sample size | Treatment | Baseline | Endpoint | Change at Endpoint (Mean/SD) | % reduction from baseline | LANTUS-AMARYL | |
|---|---|---|---|---|---|---|---|---|---|
| Triglycerides | 300-500 | 44 | LANTUS | 362 | 240 | −122.5/102 | 34% | 16% | 52.5 |
| | | 50 | AMARYL | 390 | 321 | −70.0/111 | 18% | | |
| | 500-1000 | 25 | LANTUS | 661 | 409 | −252.0/208 | 38% | 5% | 34.4 |
| | | 16 | AMARYL | 662 | 445 | −217.6/188 | 33% | | |
| | 300-1000 | 69 | LANTUS | 470 | 301 | −169.4/160 | 36% | 13% | 63.6 |
| | | 66 | AMARYL | 459 | 350 | −105.8/147 | 23% | | |
| | 200-500 | 124 | LANTUS | 288 | 232 | −56.3/117 | 25% | 13% | 21.7 |

TABLE 1-continued

Summary of lipid data for LANTUS (from 4002 Study) and AMARYL (from two AMARYL studies with placebo control)

| Variable | Subgroup by TG baseline range | Sample size | Treatment | Baseline | Endpoint | Change at Endpoint (Mean/SD) | % reduction from baseline | LANTUS-AMARYL | |
|---|---|---|---|---|---|---|---|---|---|
| | | 129 | AMARYL | 299 | 265 | −34.6/107 | 12% | | |
| Non-HDL | 300-500 | 44 | LANTUS | 180 | 152 | −27.6/36 | 15% | 12% | 21.9 |
| Cholesterol | | 50 | AMARYL | 203 | 198 | −5.7/32 | 3% | | |
| Total | 500-1000 | 25 | LANTUS | 186 | 171 | −14.1/35 | 8% | −2% | −9.0 |
| | | 16 | AMARYL | 224 | 200 | −23.1/35 | 10% | | |
| | 300-1000 | 69 | LANTUS | 181 | 163 | −18.5/40 | 10% | 5% | 8.6 |
| | | 66 | AMARYL | 209 | 198 | −9.9/33 | 5% | | |
| | 200-500 | 124 | LANTUS | 167 | 155 | −12.5/33 | 7% | 4% | 5.8 |
| | | 129 | AMARYL | 197 | 191 | −6.7/30 | 3% | | |
| HDL | 300-500 | 44 | LANTUS | 40 | 40 | 0.1/6 | | | |
| | | 50 | AMARYL | 36 | 37 | 1.2/6 | | | |
| | 500-1000 | 25 | LANTUS | 33 | 36 | 3.1/7 | | | |
| | | 16 | AMARYL | 37 | 39 | 1.6/6 | | | |
| | 300-1000 | 69 | LANTUS | 37 | 38 | 1.2/7 | | | |
| | | 66 | AMARYL | 36 | 37 | 1.3/6 | | | |
| | 200-500 | 124 | LANTUS | 42 | 41 | −0.6/8 | | | |
| | | 129 | AMARYL | 38 | 39 | 1.2/5 | | | |
| LDL | All | 306 | LANTUS | 113 | 110 | −3.3/27 | | | |
| | | 272 | AMARYL | 142 | 140 | −1.5/23 | | | |

The lipid-lowering effects of metformin are variable depending on the study and clinical setting, but while the TG-lowering and HDL-increasing effects of metformin are generally superior to SU, they do not exceed the effects of insulin quoted above. Thiazolidinediones (TZDs) differ in their effects—pioglitazone is associated with notable beneficial effects on the abnormalities of DDL, whereas rosiglitazone seems to have almost no effect on these parameters (confirmed significantly inferior to Lantus LANTUS (insulin glargine) in Study 4014, which compared Lantus® LANTUS (insulin glargine) and rosiglitazone in type 2 diabetic patients already treated with other oral antidiabetic drugs—see Table 2 below).

oral antidiabetic agents because of a fear of hypoglycemia from the use of insulin in this population. The novel development is the availability of Lantus® LANTUS (insulin glargine), the first truly basal insulin, which by virtue of its flat pharmacokinetic profile and 24-hour duration of action, can supply a steady insulin effect with low risk for hypoglycemia due to the lack of a pronounced peak effect. Because of this, insulin treatment of the diabetic patient previously treated with lifestyle measures only, is possible, and thus insulin treatment of patients in this category with pronounced diabetic dyslipidemia is possible, to reduce their elevated blood lipid values as well as their elevated blood glucose values.

TABLE 2

Summary of lipid data for LANTUS and AVANDIA from Study 4014

| Variable | Subgroup by TG baseline range | Sample size | Treatment | Baseline | Endpoint | Change at Endpoint (Mean/SD) | % reduction from baseline | LANTUS-AVANDIA | |
|---|---|---|---|---|---|---|---|---|---|
| Triglycerides | 300-500 | 11 | LANTUS | 380 | 277 | −102.8/130 | 27% | 18% | 68.5 |
| | | 18 | AVANDIA | 376 | 341 | −34.3/159 | 9% | | |
| | 500-1000 | 4 | LANTUS | 817 | 494 | −323.3/268 | | | |
| | | 3 | AVANDIA | 572 | 649 | 77.0/548 | | | |
| | 200-500 | 37 | LANTUS | 285 | 234 | −50.2/101 | 18% | 18% | 47.7 |
| | | 51 | AVANDIA | 294 | 291 | −2.5/133 | 0.1% | | |
| Non-HDL | 300-500 | 11 | LANTUS | 156 | 150 | −5.9/22 | 4% | | |
| Cholesterol | | 18 | AVANDIA | 177 | 207 | 29.8/47 | −17% | | |
| Total | 500-1000 | 4 | LANTUS | 178 | 153 | −25.3/25 | | | |
| | | 3 | AVANDIA | 231 | 261 | 30.0/48 | | | |
| | 200-500 | 37 | LANTUS | 168 | 152 | −15.5/32 | | | |
| | | 51 | AVANDIA | 41 | 59 | 29.2/48 | | | |
| HDL | 300-500 | 11 | LANTUS | 32 | 34 | 2.2/4 | | | |
| | | 18 | AVANDIA | 38 | 41 | 3.8/6 | | | |
| | 500-1000 | 4 | LANTUS | 28 | 29 | 1.0/3 | | | |
| | | 3 | AVANDIA | 39 | 38 | −1.0/8 | | | |
| | 200-500 | 37 | LANTUS | 38 | 40 | 1.2/5 | | | |
| | | 51 | AVANDIA | 38 | 40 | 2.6/6 | | | |
| LDL | 200-500 | 34 | LANTUS | 115 | 111 | −4.3/34 | | | |
| | | 46 | AVANDIA | 99 | 129 | 29.7/36 | | | |

The special advantages of insulin in the treatment of diabetic dyslipidemia, which along with insulin's established effectiveness in blood glucose control, suggest that it is a preferred treatment compared to available oral antidiabetic drugs. Until recently, the drug treatment of blood glucose elevations in drug-naïve diabetic patients has consisted of In view of the data described above, treatment with long acting insulin, particularly insulin glargine, is expected to safely and effectively retard atherosclerosis progression in patients with IGF, IFG or Type 2 diabetes, particularly early Type 2 diabetes by improving glycemic control and by additional mechanisms including decreased free fatty acid production, improved control of dyslipidemia, decreased oxidative stress and increased endothelial nitric oxide availability.

Treatment with long acting insulin, particularly insulin glargine, is also expected to safely and effectively improve vascular function in patients with IGT, IFG or Type 2 diabetes, particularly early Type 2 diabetes. Long acting insulin, particularly insulin glargine, is expected to improve endothelial function based on its effects on smooth muscle cells, endothelial cells, suppression of cytokines, coagulants and increased endothelial nitric oxide synthase. Coronary endothelial dysfunction is defined as an impaired vasodilatory response to intracoronary infusion of acetylcholine (Ach) and is predictive of vascular events. Acute studies have shown that a physiological increase in the circulating insulin concentration potentiates Ach-induced vasodilation.[43] In another study, after two months of insulin therapy, patients with type 2 diabetes saw an increase in the blood flow response to Ach and restored the ability of insulin to acutely potentiate Ach-induced vasodilation.[44]

Finally, patients with diabetes have been shown to have increased left ventricular mass and abnormalities in left ventricular (LV) diastolic and systolic function, often referred to as diabetic cardiomyopathy. These abnormalities may extend also to patients with "mild" prediabetic hyperglycemic disorders. Treatment with long acting insulin, particularly insulin glargine, is expected to prevent an increase in LV mass and improve or prevent an increase in both LV diastolic and systolic function in patients with IGT, IFG or Type 2 diabetes, particularly early Type 2 diabetes.

Treatment with long acting insulin, particularly glargine, is expected to prevent an increase in carotid intimal thickness of the extracranial carotid artery. Measurement of carotid intimal thickness is a highly reproducible technique, which correlates with risk factors for atherosclerosis progression in coronary disease and stroke (N Engl J Med. 1999; 340:14-22). Angiotensin-converting enzyme inhibitors and the insulin sensitizing thiazolidinediones are all agents which have been shown to reduce carotid intimal thickness in placebo controlled trials (Circulation. 2001; 103:919-925; J Clin Endocrinol Metab 1998; 83:1818-1820; J Clin Endocrinol Metab 2001; 86:34552-3456).

The amount of long acting insulin necessary to achieve the desired biological effect depends on a number of factors, for example the specific long acting insulin chosen, the intended use, the mode of administration and the clinical condition of the patient. The daily dose of insulin glargine is generally in the range from 2 to about 150 IU per day. More preferred is a daily dose in range in the range of 2 to about 80 IU per day. Even more preferred is a daily dose in the range of about 2 to about 40 IU per day.

As used herein, the term "patient" means a warm blooded animal, such as for example rat, mice, dogs, cats, guinea pigs, and primates such as humans.

As used herein, the term "treat" or "treating" means to alleviate symptoms, eliminate the causation of the symptoms either on a temporary or permanent basis, or to prevent or slow the appearance of symptoms of the named disorder or condition.

As used herein, the term "effective dosage" means a quantity of the compound which is effective in treating the named disorder or condition.

As used herein, the term "long acting insulin" is an insulin analog that is a long acting (up to 24-hour duration of action) blood glucose lowering agent. Such long acting insulins include, but are not limited to, Lantus® LANTUS (insulin glargine), NPH, Lente® LENTE human insulin zinc suspension (rDNA origin), Ultralente® ULTRALENTE human insulin extended zinc suspension (rDNA origin), and Semilente® SEMILENTE (prompt insulin zinc suspension).

As used herein, the term "early Type 2 diabetes" is defined as a FPG≧126 mg/dL (7.0 mM) or a PPG≧200 mg/dL (11.1 mM), or a previous diagnosis of diabetes, and either:
1) on no pharmacological treatment (while ambulatory) for at least 10 weeks prior to screening with screening glycated hemoglobin<150% of the upper limit of normal for the laboratory (e.g. <9% if the upper limit is 6%) or
2) taking one OAD (from among sulfonylureas, biguanides, thiazolidinediones, alpha-glucosidase inhibitors, and meglitinides) at a stable dose for at least 10 weeks at the time of screening (or for the 10 weeks prior to hospitalization if identified while hospitalized for a CV event), with screening glycated hemoglobin<133% of the upper limit of normal for the laboratory (e.g. <8% if the upper limit is 6%) if taking this medication at half-maximum dose or greater, and glycated hemoglobin<142% of the upper limit of normal for the laboratory (e.g. <8.5% if the upper limit is 6%) if taking this medication at less than half-maximum dose.

The citation of any reference herein should not be construed as an admission that such reference is available as "Prior Art" to the instant application.

Various publications are cited herein, the disclosures of which are incorporated by reference in their entireties.

REFERENCES

1. Stamler J, Vaccaro 0, Norton J D, Wentworth D. Diabetes, other risk factors, and 12-yr cardiovascular mortality for men screened in the Multiple Risk Factor Intervention Trial. Diabetes Care 1993; 16: 434-44.
2. Stratton I M, Adler A I, Nell A W, Matthews D R, Manley S E, Cull C A, et al. Association of glycaemia with macrovascular and microvascular complications of type 2 diabetes (UKPDS 35): prospective observational study. BMJ 2000; 321: 405-412.
3. Coutinho M, Wang Y, Gerstein H C, Yusuf S. The relationship between glucose and incident cardiovascular events. Diabetes Care 1999; 22(2): 233-240.
4. Khaw K-T, Wareham N, Luben R, Bingham S, Oakes S, Welch A, et al. Glycated haemoglobin, diabetes, and mortality in men in the Norfolk cohort of European Prospective Investigation of Cancer and Nutrition (EPIC-Norfolk). BMJ 2001; 322: 15-18.
5. Gerstein H C, Yusuf S. Dysglycaemia and risk of cardiovascular disease. Lancet 1996; 347: 949-50.
6. Expert Committee on the Diagnosis and Classification of Diabetes Mellitus. Report of the expert committee on the diagnosis and classification of diabetes mellitus. Diabetes Care 1997; 20(7): 1183-97.
7. The Diabetes Control and Complications Trial Research Group: the effect of intensive treatment of diabetes on the development and progression of long-term complications in insulin-dependent diabetes mellitus. N Engl J Med 1993; 329: 977-86.
8. Shichiri M, Kishikawa H, Ohkubo Y, Wake N. Long-term results of the Kumamoto study on optimal diabetes control in type 2 diabetic patients. Diabetes Care 2000 April; 23(Supp2): B21-9.

9. Reichard P, Nilsson B-Y, Rosenqvist U. The effect of long-term intensified insulin treatment on the development of microvascular complications of diabetes mellitus. N Engl J Med 1993; 329: 304-9.
10. Laakso M. Glycemic control and the risk for coronary heart disease in patients with non-insulin-dependent diabetes mellitus. Annals Int Med 1996; 124 (1 pt 2): 127-130.
11. Moss S E, Klein R, Klein B E K, Meuer S M. The association of glycemia and cause-specific mortality in a diabetic population. Arch Int Med 1994; 154: 2473-9.
12. Jackson C A, Yudkin J S, Forrest R D. A comparison of the relationships of the glucose tolerance test and the glycated haemoglobin assay with diabetic vascular disease in the community. The Islington Diabetes Survey. Diabetes Res Clin Pract 1992; 17: 111-123.
13. Wei M, Gaskill S P, Haffner S M, Stem M P. Effects of diabetes and level of glycemia on all-cause and cardiovascular mortality. The San Antonio Heart Study. Diabetes Care 1998; 21 (7): 1167-72.
14. UKPDS Group. Intensive blood-glucose control with sulphonylureas or insulin compared with conventional treatment and risk of complications in patients with type 2 diabetes (UKPDS 33). Lancet 1998; 352: 837-53.
15. deVegt F, Dekker J M, Ruhe H G, Stehouwer C D A, Nijpels G, Bouter L M, et al. Hyperglycaemia is associated with all-cause and cardiovascular mortality in the Hoorn population: the Hoorn Study. Diabetologia 1999; 42: 926-931.
16. Simmons L A, McCallum J, Friedlander Y, Simmons J. Fasting plasma glucose in non-diabetic elderly women predicts increased all-cause mortality and coronary heart disease risk. Aust NZ Med 2000; 30: 41-7.
17. Bjomholt J V, Nitter-Hauge S, Erikssen G, Jervell J, Aaser E, Erikssen J, et al. Fasting blood glucose: an underestimated risk factor for cardiovascular death. Diabetes Care 1999; 22: 45-9.
18. Balkan B, Shipley M, Jarret R J, Pyorala K, Pyorala M, Forhan A. et al. High blood glucose concentration is a risk factor for mortality in middle-aged nondiabetic men. 20-year follow-up in the Whitehall Study, the Paris Prospective Study, and the Helsinki Policemen Study. Diabetes Care 1998; 21: 360-367.
19. Balkan B, Bertrais S, Dugimetiere P, Eschwege E. Is there a glycemic threshold for mortality risk? Diabetes Care 1999; 22(5): 696-9.
20. Barzilay J I, Spiekennan C F, Wahl P W, Kuller L H, Cushrnan M, Furberg C D, et al. Cardiovascular disease in older adults with glucose disorders: comparison of American Diabetes Association criteria for diabetes mellitus with WHO criteria. Lancet 1999; 354: 622-5.
21. Diabetes Prevention Research Group: Reduction in the evidence of Type 2 Diabetes with life-style intervention or metformin. N Engl J Med 346:393-403, 2002.
22. Passikivi J, Walberg F. Preventive tolbutamide treatment and arterial disease in mild hyperglycaemia. Diabetologia 1971; 7: 323-27.
23. Sartor G, Schersten B, Carlstrorn S, Melander A, Norden A, Persson G. Ten-year follow-up of subjects with impaired glucose tolerance. Prevention of diabetes by tolbutamide and diet regulation. Diabetes 1980; 29: 41-49.
24. Malmberg K, Ryden L, Hamsten A, Herlitz I, Waldenstrom A, Wedel H. Mortality prediction in diabetic patients with myocardial infarction: experiences from the DIGAMI study. Cardiovascular Research 1997; 34: 248-253.
25. Van den Berghe G, Wouters P, Weekers F, Verwaest C, Bruyninckx F, Schetz M et al. Intensive insulin therapy in critically ill patients. N Engl J Med 2001; 345: 1359-67.
26. Baron A D. Vascular reactivity. Am I Cardiol 1999; 84(IA): 25J-27J.
27. Aljada A, Dandona P. Effect of insulin on human aortic endothelial nitric oxide synthase. Metabolism 2000; 49: 147-50.
28. Taylor P D, Oon B B, Thomas C R, Poston T, Poston L. Prevention by insulin treatment of endothelial dysfunction but not enhanced noradrenaline-induced contractility in mesenteric resistance arteries from streptozotocin-induced diabetic rats. Br J Pharmacol 1994; 111(1): 35-41.
29. Dandona P, Aljada A, Mohanty P, Ghanim H, Hamouda W, Assian E, Ahmad S. Insulin inhibits intranuclear nuclear factor kB and stimulates IkB in mononuclear cells in obese subjects: evidence for an anti-inflammatory effect? J Clin Endocrin; luly 2001; 3257-3265.
30. American Diabetes Association: Clinical Practice Recommendations. Position Statement, Diabetes Mellitus and Exercise. Diabetes Care 2001 24 (Suppl 1): 551-5 31. Diabetes Prevention Research Group: Reduction in the evidence of Type 2 Diabetes with life-style intervention or metformin. N Engl J Med 346:393-403, 2002.
32. Diabetes Prevention Research Group: Reduction in the evidence of Type 2 Diabetes with life-style intervention or metformin. N Engl J Med 346:393-403, 2002.
33. Tuomilehto J, Lindstrom J, Eriksson J G, Valle T T, Hamalainen H, Ilanne-Parikka P, Keinanen-Kiukaanniemi S, Laakso M, Louheranta A, Rastas M, Salminen V, Uusitupa M; Finnish Diabetes Prevention Study Group. (Department of Epidemiology and Health Promotion, National Public Health Institute, Helsinki, Finland. jaakko.tuomilehtoktl)
Prevention of type 2 diabetes mellitus by changes in lifestyle among subjects with impaired glucose tolerance. N Engl J. Med. 2001 May 3; 344(18):1343-50.
34. Murray F T, Ziman B, McLean P A, DeNoga A, Albisser A M, Leibel B S, et. al. The metabolic response to moderate exercise in diabetic man receiving intravenous and subcutaneous insulin. *Journal of Clinical Endocrinology and Metabolism* 1977 4: 708-720
35. Herz M, Profozic V, Arora V, Smircik-Duvnjac L, Kovacevic I, Boras J et al. Effects of a fixed mixture of 25% insulin lispro and 75% NPL on plasma glucose during and after moderate physical exercise in patients with type 2 diabetes. *Current medical research and opinions* 2002 18: 188-93
36. Rabasa-Lhoret R, Bourque J, Ducros F, Chiasson, J-L. Guidelines for premeal insulin dose reduction for postprandial exercise of different intensities and durations in type 1 diabetic subjects treated intensively with a basal-bolus insulin regimen (ultralente-lispro). *Diabetes Care* 2001 24: 625-30
37. Hernandez J M, Moccia T, Fluckey J D, Ulbrecht J S, Farrell P A. Fluid snacks to help persons with type 1 diabetes avoid late postexercise hypoglycemia. *Medicine and Science in Sports and Exercise* 2000 32: 904-10.
38. Riddle M, Rosenstock J, Gerich J. The Treat-to-Target trial. *Diabetes Care* 2003 26:
39. Lepore M, Pampanelli S, Fanelli C, Porcellati F, Bartocci L, DiVincenzo A et al. Pharmacokinetics and pharmacodynamics of subcutaneous injection of long-acting human insulin analog glargine, NPH insulin, and human ultralente insulin, and continuous subcutaneous infusion of insulin lispro. *Diabetes* 2000 49: 2142-8.
40. Chiasson J-L, Josse R G, Gomis R, Hanefeld M, Karasik A, Laakso M. Acarbose treatment and the risk of cardiovascular disease and hypertension in patients with Impaired Glucose Tolerance. JAMA 2003 290: 486-94

41. Cryer P, Davis s, Shamoon H. Hypoglycemia in diabetes. *Diabetes Care* 2003 26: 1902-12
42. The UKPDS Research Group. A 6-year, m randomized, controlled trial comparing sulfonylurea, insulin, and metformin therapy in patients with newly-diagnosed type 2 diabetes that could not be controlled with diet therapy. *Ann Int Med* 1998 128: 165-75
43. Taddei S, Virdis A, Mattei P, Natali A, Ferrannini E, Salvetti A. Effect of insulin on acetylcholine-induced vasodilation in normotensive subjects and patients with essential hypertension. Circulation 1995; 92:2911-2918.
44. Rask-Madsen C, Ihlemann N, Krarup T, Christiansen E, Kober L, Nervil K C, Torp-Pedersen C. Insulin therapy improves insulin-stimulated endothelial function in patients with Type II diabetes and ischemic heart disease. Diabetes. 2001; 50:2611-2618.
45. Azen S P, Peters R K, Berkowitz K, Kjos S, Xiang A, Buchanan T A.
(Department of Medicine, University of Southern California (USC) School of Medicine 90033, USA.)
TRIPOD (TRoglitazone In the Prevention Of Diabetes): a randomized, placebo-controlled trial of troglitazone in women with prior gestational diabetes mellitus; Control Clin Trials. 1998 April; 19(2):217-31.

What is claimed is:

1. A method of preventing an increase in left ventricular mass in a patient diagnosed with a disease or condition selected from the group of impaired fasting glucose (IFG) and impaired glucose tolerance (IGT), comprising administering to said patient a therapeutically effective dosage of a long acting insulin.
2. The method according to claim 1 wherein the long acting insulin is insulin glargine.
3. The method according to claim 2 wherein the effective dosage is in the range of about 2 to about 150 IU per day.
4. The method according to claim 3 wherein the effective dosage is in the range of about 2 to about 80 IU per day.
5. The method according to claim 4 wherein the effective dosage is in the range of about 2 to about 40 IU per day.
6. A method of preventing an increase in carotid intimal thickness in a patient diagnosed with a disease or condition selected from the group of impaired fasting glucose (IFG) and impaired glucose tolerance (IGT), comprising administering to said patient a therapeutically effective dosage of a long acting insulin.
7. The method according to claim 6 wherein the long acting insulin is insulin glargine.
8. The method according to claim 7 wherein the effective dosage is in the range of about 2 to about 150 IU per day.
9. The method according to claim 8 wherein the effective dosage is in the range of about 2 to about 80 IU per day.
10. The method according to claim 9 wherein the effective dosage is in the range of about 2 to about 40 IU per day.

* * * * *